United States Patent [19]

Hemphill

[11] Patent Number: 4,557,720
[45] Date of Patent: Dec. 10, 1985

[54] VAGINAL APPLICATOR

[76] Inventor: Allegra D. Hemphill, 6217 Charnwood Dr., Rockville, Md. 20852

[21] Appl. No.: 619,684

[22] Filed: Jun. 11, 1984

Related U.S. Application Data

[63] Continuation of Ser. No. 434,828, Oct. 18, 1982, abandoned.

[51] Int. Cl.$^4$ ............................................. A61B 10/00
[52] U.S. Cl. .................................. 604/1; 401/77; 401/78
[58] Field of Search ............... 604/1, 2; 401/77, 78, 401/196, 202, 207, 116

[56] References Cited

U.S. PATENT DOCUMENTS

| 251,502 | 4/1879 | Bridle . |
| 493,591 | 3/1893 | Kenner ................................ 604/2 |
| 685,088 | 10/1901 | Barlow ................................ 604/1 |
| 1,711,352 | 4/1929 | Jeffreys ................................ 604/1 |
| 2,344,060 | 3/1944 | Ray . |
| 2,393,677 | 1/1946 | Gelardin ........................ 401/77 X |
| 3,586,452 | 6/1971 | Mason . |
| 3,731,682 | 5/1973 | Fielding . |
| 4,023,559 | 5/1977 | Gaskell ............................ 604/1 X |
| 4,155,991 | 5/1979 | Schopflin et al. . |
| 4,157,709 | 6/1979 | Schuster et al. . |
| 4,159,718 | 7/1979 | Bower . |
| 4,165,942 | 8/1979 | Johansson . |
| 4,175,439 | 11/1979 | Laker . |
| 4,177,811 | 12/1979 | Alvarez ............................ 604/1 |

FOREIGN PATENT DOCUMENTS

| 114619 | 10/1929 | Austria ............................ 604/1 |

Primary Examiner—John D. Yasko
Assistant Examiner—Christa K. Scott
Attorney, Agent, or Firm—Allegra D. Hemphill; F. Erich Hemphill; Gardner, Vivian C.

[57] ABSTRACT

A disposable vaginal refreshener or swab comprised of an outer container for enclosing an inner, fairly rigid core member about which an adsorbent layer is secured. The outer container when removed, exposes the adsorbent covered member or allows that member to be moved out of the container into an operable position. The outer container also forms the handle for the disposable swab element.

2 Claims, 11 Drawing Figures

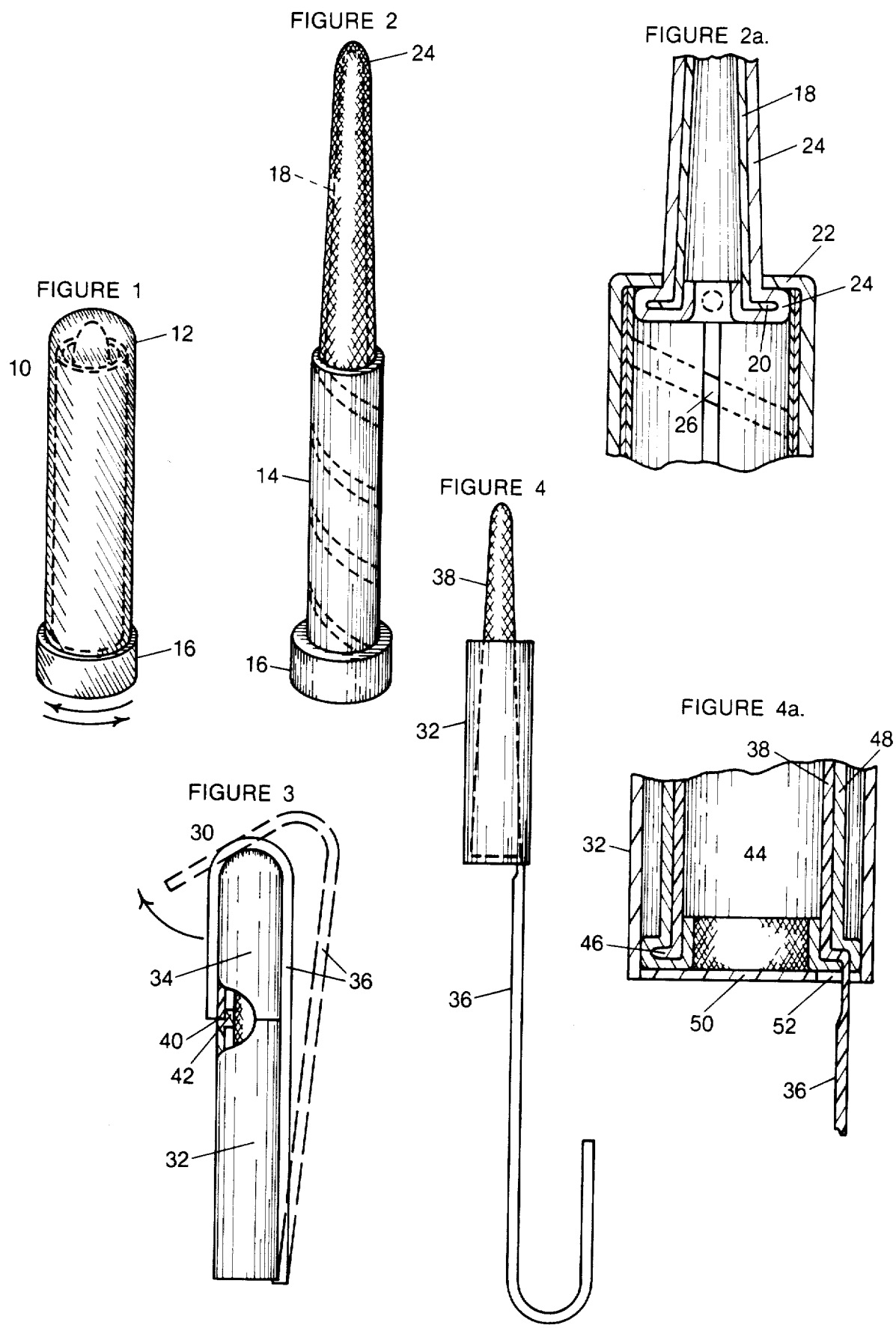

VAGINAL APPLICATOR

This application is a continuation of Ser. No. 434,828 filed Oct. 18, 1982 now abandoned.

FIELD OF THE PRESENT INVENTION

The present invention relates to vaginal swabs and refreshners.

BACKGROUND OF THE PRESENT INVENTION

It is well known that the vagina is a relatively long, hollow, tube like structure that extends from the cervix or the outer end of the uterus down to the labia minora. The interior of the vagina is composed of a mucous membrane and an outer, smooth muscle closely attached to it. While glands are present in the vaginal lining itself, vaginal secretions can arise from the glands in the cervical canal of the uterus such as bartholin's and skene's glands. The lining of the vaginal cavity also responds to stimulation from various ovarian hormones either by building up new cell layers or by shedding old ones. Likewise, mucous is developed in the cervical canal of the uterus at other times, such as in the proliferative phase of the menstrual cycle where the endometrium thickens and its glands begin their secretion of mucous. Thus, it is well known that a variety of secretions develop varying amounts of mucous and other material as the result of a variety of factors and conditions.

Normally, such secretions are clean but occassionally debris in the form of blood or from the deposition of seminal fluid can accumulate. Accordingly, it is desirable at times to be able to have a convenient disposable swab or refreshner available for purposes of cleansing the vaginal area or for purposes of adding or treating the vaginal area with fragrances, medications, germicides or deodorants.

Many types of vaginal devices have been suggested including plunger type devices as in Rogers, U.S. Pat. No. 1,256,831, swabs as in U.S. Pat. No. 3,228,393, or foam type devices directly formed in their outer container as in Ravel, U.S. Pat. No. 4,260,570.

SUMMARY OF THE PRESENT INVENTION

I have found that a truly portable, convenient and disposable internal vaginal cleaning device or refreshner is not available, especially one that is small, compact, easily usable and very simply constructed. The devices such as disclosed in the Rogers patent are cumbersome and not easily disposable. I have found that a device such as disclosed by Ravel is not convenient to use as the device does not provide a sufficiently long handle structure in order to manipulate the swab itself to produce appropriate and needed cleaning. Further, the foam or sponge-like exteriors from which some vaginal swabs or applicators are comprised as in Ravel are not sufficiently adsorbent to produce the necessary and appropriate cleaning required. Rather, such devices tend to collect mucous and other vaginal fluids only on their outer surfaces as they do not have the absorbency needed to provide the amount of fluid collection and removal or to hold and apply the proper amount of material that should be used for proper treatment, as is actually desired or necessary.

My device, as set forth herein, is comprised of an outer container, the various embodiments of which allow that container, or at least a part thereof, to form the handle structure for the swab, with that handle providing both the protection for the swab while packaged and a handle during use to provide better control over swab during such use.

The swab portion is preferably comprised of fairly rigid inner core member, constructed either in segments or as a one piece unit, over which a thick, gauze type adsorbent pad or layer is secured. In one embodiment, the rigid structure on which the pad is secured is retractable into and extendable from an outer container in which it is held by means of twisting a rotatable bottom thereof in a manner similar to raising and lowering a lipstick. In a second embodiment, the outer container is held together by means of a flexible strap or lever-type handle with that strap or handle serving to provide means for extending the swab from its retracted to its raised operative position. In another embodiment, the outer container is essentially peeled away from its enclosing or protecting relationship about the swab itself with at least part of the outer container forming the handle structure at the base of the thus exposed swab.

Other objects, features, and characteristics of the present invention, as well as the methods and operation and functions of the related elements of the structure, and to the combination of parts and economies of manufacture, will become more apparent upon consideration of the following detailed description and the appended claims with reference to the accompanying drawings, all of which form a part of this specification, wherein like reference numerals designate corresponding parts in the various figures.

BRIEF DESCRIPTION OF THE DRAWINGS

FIG. 1 is a view of a first embodiment of the present invention showing the device in its covered, closed and unextended condition;

FIG. 2 is a view of the device as in FIG. 1 in its extended, operating condition;

FIG. 2a is a diagrammatic cross-sectional view of a portion of the device shown in FIG. 2;

FIG. 3 is a side, elevational view of a second embodiment of the present invention in its closed condition;

FIG. 4 is a side, elevational view of device shown in FIG. 3 with the top having been removed, prior to the swab being raised to its operative position;

FIG. 4a is a diagrammatic cross-sectional view of a portion of the bottom of the device shown in FIG. 4;

DETAILED DESCRIPTION OF THE PREFERRED EMBODIMENTS OF THE PRESENT INVENTION

Figure 5:
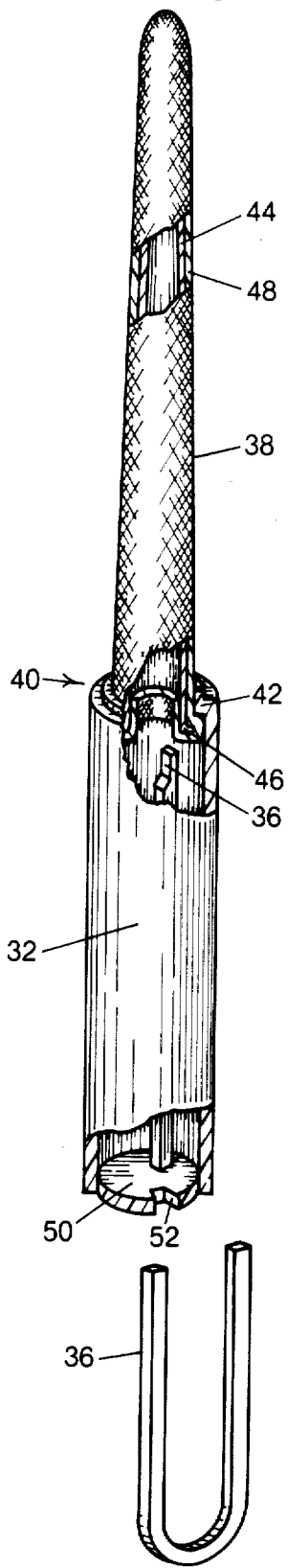
FIG. 5 is a side, elevational view of the device shown in FIGS. 3 and 4 in its raised operative condition with portions having been cut away or omitted for clarity.

As explained above, the present invention is designed to dry or absorb material in the internal vaginal area when one observes a discharge or lubrication building up to the point that cleansing is either desired or required. Alternatively, the swab can be used as an applicator for a variety of products or medicants and it can either be pre-impregnated therewith or such materials could be applied once the swab was unpackaged. It should be understood that the adsorbent gauze material and the swab element is contemplated as being sterile when packaged. Likewise, it is important that the device be extremely compact and easily manufactured so as to be both portable and disposable rendering it easily carriable and usable.

Turning first to FIGS. 1, 2 and 2a, the device is comprised of an outer housing, generally indicated at 10, with that outer housing being comprised of an exterior cover 12, an internal tubular member 14 and rotatable base 16. The swab itself is comprised of an internal and preferably hollow core member 18 which as shown in FIG. 2a preferably has a flange 20 integrally formed therewith and extending about its base. Flange 20 cooperates with a radially inwardly extending flange 22 at the top of tube 14 so that when core member 18 is in its fully extended position, as shown in FIG. 2, flanges 20 and 22 will abut one another and prevent further movement as shown in FIG. 2a.

An outer gauze adsorbent layer 24 is secured to core 18 by any convenient means, preferably by a medically inert adhesive. It is also preferred that gauze 24 extend over or around flange 20 at the base of core member 18. Accordingly, when core 18 is in its fully raised condition, gauze 24 will be effectively clamped between flanges 20 and 22.

The operation of this structure, in order to raise core 18 from the position shown in FIG. 1 to the erected or extended position shown in FIG. 2, is accomplished by a conventional helical cam and guide slot arrangement, generally indicated at 26 in FIG. 2a. Such mechanisms, for example, are shown in Coryel, U.S. Pat. No. 1,504,216, or Davis, U.S. Pat. No. 3,677,654, both of which are exemplary of conventional well known mechanisms for raising and lowering lipsticks. Thus, by rotating base 16 it is possible to raise and lower core 18 and the attached gauze material 24.

Figure 7:
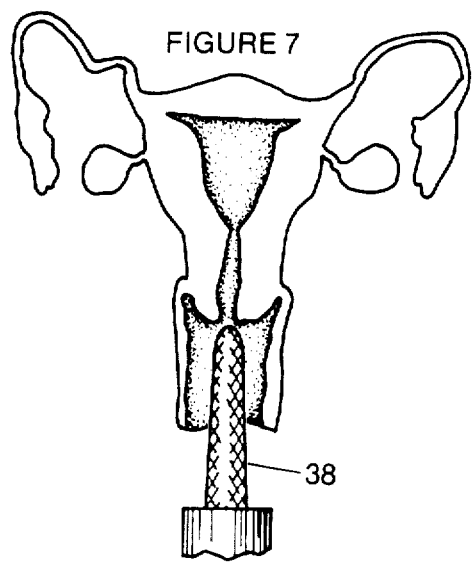
FIG. 7 is diagrammatic, cross-sectional view of the female reproductive system showing the area in which the present device is used.

With reference to FIG. 7, the average vaginal cavity is approximately 9 cm (3.5 inches) long. Accordingly, I prefer to have the swab, gauze material 24 and likewise core 18 be approximately 4 inches long. Container 14 accordingly must be approximately 4 inches in length in order to effectively receive core 18 and the gauze material 24 therein when core 18 is retracted, as shown in FIG. 1. I have found that a cover having a total length of approximately 4 inches is sufficient to completely encase container 14 above base 16.

The container is preferably made from a moldable plastic material, such as polyethylene or any one of the other polyolefins or from thermoplastics. Core 18 can be made from the same material. I prefer to have the adsorbent material 24 be comprised of a cotton or cotton/polyester gauze. However, it is important to employ a highly absorbant material and, accordingly, any such materials could be used as the absorbant material 24.

As an alternative method of raising and lowering swab 24, the interior of core 18 can be provided with suitable threads and a suitably corresponding threaded rod (not shown) could be attached to the rotatable base 16. As base 16 was rotated it would likewise rotate the threaded rod which would in turn, rotate inside core member 18 causing that core member to be raised or lowered depending upon the position of the core member relative to that threaded rod and the direction in which base 16 was rotated.

Turning now to FIGS. 3-5, the second embodiment of the present invention is comprised of an outer container, generally indicated at 30, which is comprised of a hollow base container 32, an exterior upper cover 34, a flexible retaining clamp member 36 and a swab member, generally indicated at 38. A flanged joint 40 is provided between base 32 and cover 34 in order to assure that the joint area is securely formed and to likewise assure their correct and desired relative positioning. If desired, a snap-type interconnection could be employed between cover 34 and base 32 as an added measure to work along with clamp member 36 to hold cover 34 in place. As shown in FIG. 3, the device is in its closed position and retaining clamp 36 is in place extending over cover 34.

Turning next to FIGS. 4a and 5a portion of the internal structure at the bottom of the device is set forth diagrammatically in cross-section in FIG. 4a where as the device in its extended condition ready for use is shown in FIG. 5. As shown in FIG. 5, the outer container 32 is provided along its upper periphery with an inwardly extending annular flange 42. Swab member 38 is respectively comprised of an internal core member 44 which is preferably formed in a one piece manner from a moldable plastic material such as, for example, polyethylene, and is formed with a bottom flange 46 as shown in both FIGS. 4a and 5. Affixed thereto is an outer sheath 48 of absorbable material and as shown, this sheath 48 preferably extends around and is affixed to core 44 adjacent the base thereof. As was true with the first embodiment, I prefer to use a medically inert adhesive for this purpose although other methods could be used to securely attach the gauze sheath 48 to core 44 in a manner that it extends over or around flange. Clamp 36 is preferably integrally formed with core 44 and is integrally hinged at a predetermined point along the bottom peripheral edge of that core member. The location where clamp member 36 is hinged to core 44 is predetermined so that when core 44 is retracted within the hollow container 32, clamp 36 can be pivoted up to its closed position extending about cover 34 as shown in FIG. 3, thereby securing core 44 within container 32 with the upper loop portion of clamp member 36 serving to hold cover 34 in place.

With reference specifically to FIG. 4, retaining member 36 has been rotated to its full pivoted unlocked condition and cover 34 has been removed thereby exposing the upper portion of swab 38. By pushing upward on member 36, the inner core 44 will be moved upwardly within container 32 thereby fully exposing swab member 38 as shown in FIG. 5. In the condition shown in FIG. 5, both the container 32 and the remaining portion of member 36 extending therebelow will act as a handle for the user to grasp onto when using the device.

In order to securely close the container to keep swab 38 sterile is to provide a bottom 50 on the lower container 32 in which a suitable passageway or opening 52 is provided through which member 36 can pass. It may be otherwise desirable to close or seal the opening 52 of container 32. This can be accomplished by a variety of sealing methods once the assembly is connected together. Preferably, a bottom member 50 is separately formed with a suitable cutout forming opening 52 with bottom member 50 snapping into place within the bottom confines of container 32 following insertion of swab 38 and member 36 into container 32.

Figure 6:
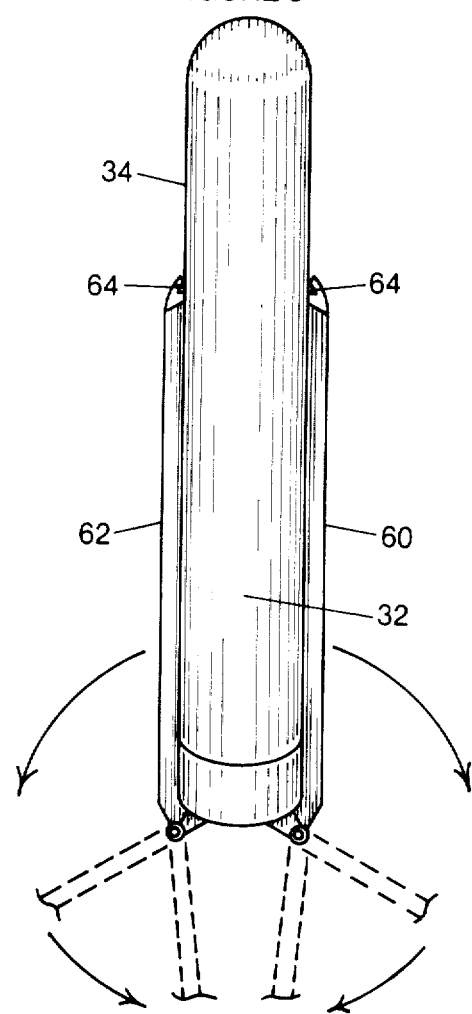
FIG. 6 is a side, elevational view of still another embodiment of the present invention showing an additional handle structure that can be located on the exterior case.

In FIG. 6, another embodiment of the present invention is shown. The cover 34' extends along the full length of the internal core supporting the gauze or adsorbent pad assembly which can be similar to the structure set forth in FIGS. 3–5 without member 36 attached thereto. In this instance, the cover itself 34' can itself snap in place with respect to the lower container 32' so that a retaining clip or other retaining device would not be required. However, in order to provide sufficient leverage for handling the device when in use and to aid in securing cover 34' to base 32', one or two handles, as indicated at 60 and 62, could be provided on the sides of outer container formed from cover 34' and lower container 32'. These handles can be integrally molded together with lower container 32' and initially held in an upright condition by means of breakable bands indicated at 64.

Figure 8:
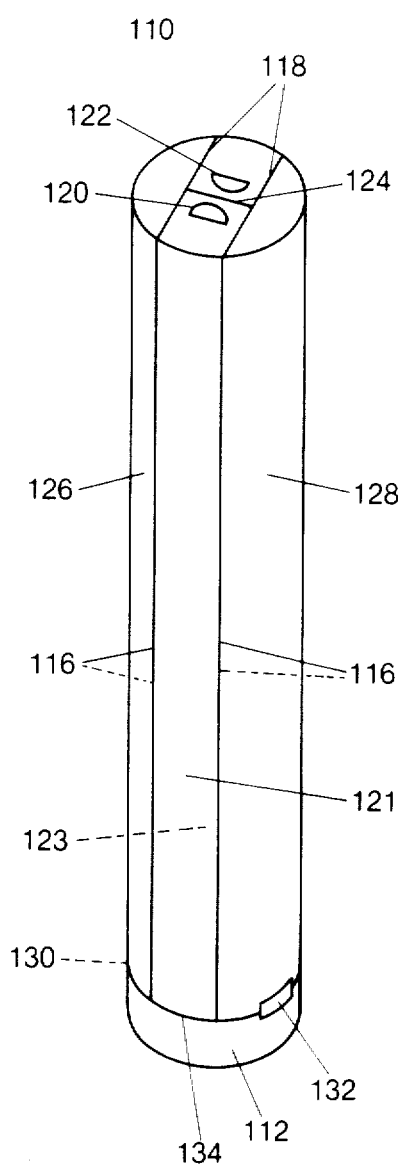
FIG. 8 is a diagrammatic, perspective view of still another embodiment of the present invention in its closed and sealed condition.
Figure 9:
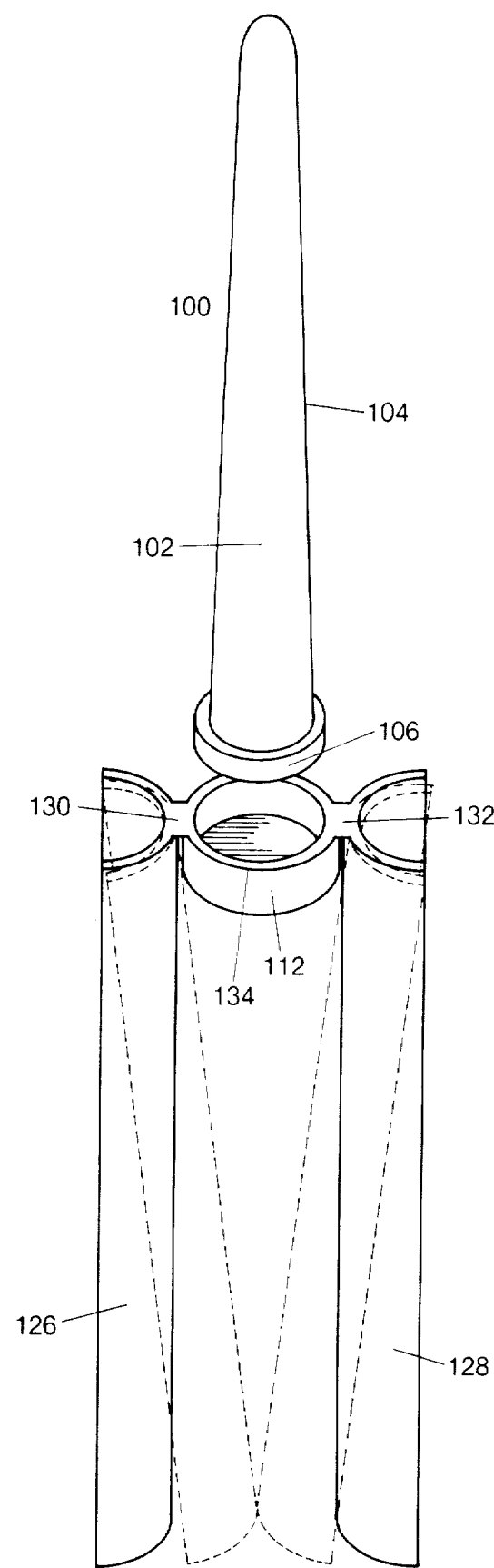
FIG. 9 is diagrammatic, perspective view of the device shown in FIG. 8 in its opened and ready to use condition.

Turning now to the last embodiment, as shown in FIGS. 8 and 9, the swab is generally indicated at 100 in FIG. 9 and is comprised of a core 102 covered by a gauze layer 104. An outer container is generally indicated at 110. Core 102 is separately formed so as to have a base formed as an annular band or ring 106. Core member 102 can be formed either as a solid structure or preferably with a hollow interior. As in the other embodiments, absorbant gauze material 104 is secured about the exterior surface of core 102 but not about annular band 106. In FIG. 9, the device is shown in its open, ready-to-use position whereas in FIG. 8, the device is shown in its closed and sealed condition. The cover or outer case 110 is comprised of an annular band or ring 112 at the base thereof together with an upper, portion generally indicated at 114. It should be understood that the annular band or ring 106 of core member 102 has an outer diameter which is at least equal to the inner diameter of band 112 so that the two can fit thereby allowing core 102 to be secured within band 112 by a suitable adhesive following their formation and the application of gauze 104. Outer container 110 is formed in its closed condition so that following insertion of core 102 therein the swab will be completely formed. However, the bottom of the resulting structure could be closed by a separate member (not shown) that would likewise fit within or over the base of band 112.

In FIG. 8, the outer container 110 is shown in its closed condition and it should be noted that container 110 is comprised of a plurality of segments defined by a plurality of sets of frangible seams. The first set of four frangible seams 116 extend axially along the side walls of the container thereby defining two opposed vertically extending strips 121 and 123 of the side wall therebetween. They also define part of container segments 126 and 128 as will become clear below. A second set of frangible seams 118 extend across the top of container 110 and connect opposing pairs of seams 116 together. An additional seam 124 extends perpendicularly between the center of seams 118 on the very top of the container. Tabs 120 and 122 are provided adjacent each side of seam 124 and will be used to pull open seam 124 and to thereby open container 110.

Another frangible seam 134 is provided between band 112 and the upper portion 114 with seam 134 defining the upper edge of band 112 and the bottom edge of upper portion 114. Two portions of that seam are thickened and, therefore, are non-frangible so that they respectively form hinges 130 and 132. The remaining portions of seam 134 are frangible and subject to being severed or broken when container 110 is opened. Seams 116, 118, 124 and 134 together serve to define sections 121, 123, 126 and 128 as well as the size of band 112. Sections 121 and 123 will be peeled away and discarded after tabs 120 and 122 are pulled up and away from each other thereby breaking seam 124 which is followed by the severing of seams 118 and 116 and a portion of seam 134 at the juncture between sections 121 and 123 and band 112. Once sections 121 and 123 have been removed, sections 126 and 128 will remain. These sections can then be rotated, respectively, about hinges 130 and 132 thus breaking the remaining portions of frangible seam 134 which had previously joined them to band 112. This open condition of segments 126 and 128 is shown in FIG. 9 with those segments being bent so that they engage one another, as shown in phantom. This opening procedure exposes swab member 100, with segments 126 and 128 serving to provide the handle structure required for using the swab. While segments 126 and 128 have been shown as comprising cylindrical type segments, the actual design of sections 121 and 123 can be modified as desired so that the resulting shape of segments 126 and 128 can be varied. In addition, it would be possible to reinforce segments 126 and 128 in an axial direction or to provide them with another internal shape that would not interfere with the dimensions and sides of swab 100 so that when sections 126 and 128 are folded down as shown in FIG. 9 a variety of handle structures could be formed.

The core member 102 and its band 106 are preferably molded as a one-piece unit. Likewise, the cover section 110, would also be integrally molded as a one-piece unit. Once these two molded portions are obtained, the gauze material 104 can be secured to core 102 with that structure then being placed into cover 110 with band 106 being permanently secured within band 112. It is believed that the resulting structure will maintain the sterile condition of gauze 104 until tabs 120 and 122 are pulled and the opening of the container 110 is initiated.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims, which scope is to be accorded the broadest interpretation so as to encompass all such modifications and equivalent structures.

What I claim is:

1. A vaginal swab comprised of an outer housing having a closed and open end on opposing ends thereof, said housing including an annular band defining said open end and a plurality of frangible seams that together define a pair of removable members and a pair of housing segments hingably secured to said annular band following removal of said removable members, a swab core member having a predetermined exterior shape, said core member having an annular base with an outer diameter equal to the inner diameter of said annular band and an adsorbent member secured to said core member, said core member being secured within said housing so that said adsorbent member is enclosed therein.

2. A vaginal swab comprising an outer housing including an inner case member and an outer case member at least part of which is connected to and overlies said inner case member;

a core member, at least one layer of a porous material secured to said core member, and housing means for supporting and enclosing said core member, said core member being secured to said housing means, having at least two portions movable relative to one another between first and second positions for enclosing said core member when in said first position and for both exposing said core member and the said porous padding secured thereto and for forming a handle for said swab when in said second position.

* * * * *

REEXAMINATION CERTIFICATE (3712th)
United States Patent [19]
Hemphill

[11] B1 4,557,720
[45] Certificate Issued Jan. 26, 1999

[54] VAGINAL APPLICATOR

[76] Inventor: Allegra D. Hemphill, 6217 Charnwood Dr., Rockville, Md. 20852

Reexamination Request:
No. 90/004,987, May 22, 1998

Reexamination Certificate for:
Patent No.: 4,557,720
Issued: Dec. 10, 1985
Appl. No.: 619,684
Filed: Jun. 11, 1984

Related U.S. Application Data

[62] Division of Ser. No. 434,828, Oct. 18, 1982, abandoned.

[51] Int. Cl.⁶ .................................................. A61B 10/00

[52] U.S. Cl. ................................ 604/1; 401/77; 401/78

[56] References Cited

U.S. PATENT DOCUMENTS 3,973,567  8/1976  Srinivasan et al. .................. 604/386

*Primary Examiner*—John Weiss

[57] ABSTRACT

A disposable vaginal refreshener or swab comprised of an outer container for enclosing an inner, fairly rigid core member about which an adsorbent layer is secured. The outer container when removed, exposes the adsorbent covered member or allows that member to be moved out of the container into an operable position. The outer container also forms the handle for the disposable swab element.

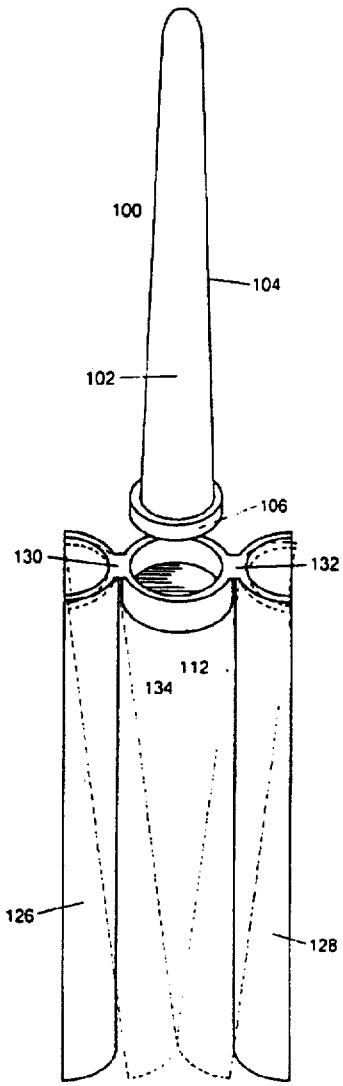

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1 and 2 is confirmed.

* * * * *